United States Patent
Shen et al.

(10) Patent No.: US 12,315,622 B2
(45) Date of Patent: May 27, 2025

(54) MEDICAL IMAGE PAGING DISPLAY SYSTEM

(71) Applicant: V5 TECHNOLOGIES CO., LTD., Hsinchu (TW)

(72) Inventors: Tzu-Kuei Shen, Hsinchu (TW); Kuo-Tung Hung, Hsinchu (TW); Chien-Ting Yang, Hsinchu (TW); Jung Chen Hsu, Hsinchu (TW)

(73) Assignee: V5MED INC., Zhubei (TW)

( * ) Notice: Subject to any disclaimer, the term of this patent is extended or adjusted under 35 U.S.C. 154(b) by 398 days.

(21) Appl. No.: 18/088,984

(22) Filed: Dec. 27, 2022

(65) Prior Publication Data
US 2024/0212830 A1    Jun. 27, 2024

(51) Int. Cl.
*G16H 30/40*     (2018.01)
*G06F 3/04812*     (2022.01)
*G16H 30/20*     (2018.01)

(52) U.S. Cl.
CPC ......... *G16H 30/40* (2018.01); *G06F 3/04812* (2013.01); *G16H 30/20* (2018.01)

(58) Field of Classification Search
CPC ..... G16H 30/40; G16H 30/20; G06F 3/04812
USPC ........................................................ 382/128
See application file for complete search history.

(56) References Cited

U.S. PATENT DOCUMENTS

| | | | |
|---|---|---|---|
| 7,202,851 B2 * | 4/2007 | Cunningham | G06F 3/038 345/163 |
| 7,324,668 B2 * | 1/2008 | Rubinstenn | H04N 23/661 382/118 |
| 8,688,747 B2 * | 4/2014 | Vincent, III | G06F 40/174 707/792 |
| 10,430,946 B1 * | 10/2019 | Zhou | A61B 5/02007 |
| 11,550,299 B2 * | 1/2023 | Cella | G06Q 30/0206 |
| 11,580,643 B2 * | 2/2023 | Huang | G06T 11/203 |
| 11,721,439 B2 * | 8/2023 | Wissel | G16H 50/30 382/128 |
| 11,862,319 B2 * | 1/2024 | Rockne | G16H 50/20 |
| 12,210,586 B2 * | 1/2025 | Weese | G06F 18/2193 |

(Continued)

FOREIGN PATENT DOCUMENTS

| | | |
|---|---|---|
| TW | I509409 B | 11/2015 |
| TW | I514862 B | 12/2015 |

(Continued)

*Primary Examiner* — William D Titcomb
(74) *Attorney, Agent, or Firm* — Birch, Stewart, Kolasch & Birch, LLP (57) ABSTRACT

A medical image paging display system includes at least one processor and a display. The processor creates a feature layer for graphical display according to at least one feature point of tissue images, and applies the feature layer to the tissue images. The feature layer includes the mark information, a page number bar, and a cursor and a feature-page mark on the page number bar. The screen shows the tissue image corresponding to the location of the cursor on the page number bar when the cursor moves on the page number bar. The screen shows the tissue image corresponding to the feature-page mark when the cursor moves to the feature-page mark. The system can quickly jump to the tissue image with a feature point and control the cursor to move several tissue images back and forth, which is helpful in observation and identification of tissue features.

12 Claims, 5 Drawing Sheets

(56) References Cited

U.S. PATENT DOCUMENTS

| | | | | |
|---|---|---|---|---|
| 2022/0328164 A1* | 10/2022 | Rogers | .................... | G16H 30/20 |
| 2022/0389511 A1* | 12/2022 | Kelley | ................ | G06F 18/2414 |
| 2023/0253095 A1* | 8/2023 | Mailhe | .................... | G16H 30/20 |
| | | | | 705/2 |
| 2024/0062563 A1* | 2/2024 | Shen | .................... | G06V 20/698 |
| 2024/0212830 A1* | 6/2024 | Shen | .................... | G06F 3/04812 |

FOREIGN PATENT DOCUMENTS

| | | |
|---|---|---|
| TW | I624175 B | 5/2018 |
| TW | I739330 B | 9/2021 |
| TW | 202145252 A | 12/2021 |

* cited by examiner

MEDICAL IMAGE PAGING DISPLAY SYSTEM

BACKGROUND OF THE INVENTION

Field of the Invention

The present invention relates to a display system for tissue images, particularly to a medical image paging display system.

Description of the Related Art

In order to accurately diagnose the disease or injury of the internal organs of the human body, or to find out the location of the lesion before performing an operation, doctors often use an imaging technology such as computerized tomography (Computed Tomography, CT) or magnetic resonance imaging (Magnetic Resonance Imaging, MRI) to scan the human body. After obtaining the images of the internal organs of the human body, the images are interpreted one by one to find out the lesions. However, hundreds of images will be obtained after each scan. Even if the doctor can lock a priority range for the predilection location of the disease based on experience, it still takes a lot of time for interpretation. On top of that, subsequent steps such as locating and labeling the lesion and measuring the size of the lesion are also very time-consuming. In addition to increasing the workload of doctors, it may also cause the doctors to ignore other lesions outside the priority interpretation range under time pressure, thereby leading to negligence in diagnosis.

Although there is currently an artificial intelligence (AI) technology for medical image-assisted interpretation, it is usually necessary to install additional medical image-assisted interpretation software before performing the AI technology. The doctors cannot use their usual image browsing software to perform AI-assisted interpretation. The implementation of AI-assisted interpretation requires additional time for the doctors to become familiar with the new software. The doctor must simultaneously execute the medical image-assisted interpretation software and the existing image browsing software and interactively compare the locations of the lesions to know the exact location of the lesion, thereby causing great inconvenience in use. Therefore, there is a need for an interpretation-assisted tool that is more convenient for doctors to use.

To overcome the abovementioned problems, the present invention provides a medical image paging display system, so as to solve the afore-mentioned problems of the prior art and satisfy requirements in the future.

SUMMARY OF THE INVENTION

The primary objective of the present invention is to provide a medical image paging display system, which creates mark information implemented with a text file, converts the mark information into a feature layer for graphical display, and applies the feature layer to tissue images, so as to overcome the problem that it is difficult to illustrate a page number bar in the conventional technology.

Another objective of the present invention is to provide a medical image paging display system, which arranges a feature-page mark on the page number bar and creates a corresponding relationship between the feature-page mark and the tissue images having a feature point. When you attempt to directly click on the feature-page mark, a cursor quickly moves to the feature-page mark and the tissue image corresponding to the feature-page mark is simultaneously displayed. As a result, a doctor does not need to search for the feature point one by one, which can improve the doctor's working efficiency.

In order to achieve the foregoing objectives, the present invention provides a medical image paging display system, which includes at least one processor and a display. The processor identifies at least one feature point of tissue images based on an artificial intelligence model and creates mark information corresponding to the feature point. The tissue images are sequentially numbered to respectively have page numbers. The processor converts the mark information into at least one feature layer for graphical display. The feature layer includes the mark information, a page number bar, and a cursor and at least one feature-page mark on the page number bar. The location of the cursor on the page number bar corresponds to the page number of the tissue image. The feature-page mark corresponds to the tissue image having the feature point. The processor applies the feature layer to the tissue images. The display is coupled to the processor. The display shows on a screen the tissue images applied with the feature layer. The display shows on the screen the tissue image corresponding to the location of the cursor on the page number bar when the cursor moves on the page number bar. The display shows on the screen the tissue image corresponding to the feature-page mark when the cursor moves to the feature-page mark.

In an embodiment of the present invention, the medical image paging display system further includes an image receiver coupled to the processor and configured to receive and transmit the tissue images provided by an external device to the processor.

In an embodiment of the present invention, the image receiver is configured to receive an image package of the tissue images.

In an embodiment of the present invention, the mark information includes the coordinates, the size, and the shape of the feature point.

In an embodiment of the present invention, the processor is configured to create and convert the page number bar, the cursor, and the feature-page mark into a part of the at least one feature layer.

In an embodiment of the present invention, the processor is configured to correspondingly mark scales on the page number bar according to the number of the tissue images.

In an embodiment of the present invention, the processor is configured to generate the feature-page mark in the location of the page number bar corresponding to the page number and establish a connection between the feature-page mark and the corresponding tissue image according to the page number of the tissue image corresponding to the feature point.

In an embodiment of the present invention, the tissue images are Digital Imaging and Communications in Medicine (DICOM) images.

In an embodiment of the present invention, the processor is configured to convert the mark information implemented with a json text file in a Grayscale Softcopy Presentation State (GSPS) into the feature layer.

In an embodiment of the present invention, the at least one feature layer comprises a plurality of feature layers having different display contents.

In an embodiment of the present invention, the medical image paging display system further includes a control interface coupled to the processor and the display and configured to control the cursor to move on the page number bar.

In an embodiment of the present invention, the display is further configured to show a layer field and the control interface is configured to control the layer field to present the selected feature layer.

Below, the embodiments are described in detail in cooperation with the drawings to make easily understood the technical contents, characteristics and accomplishments of the present invention.

DETAILED DESCRIPTION OF THE INVENTION

The technical solutions in the embodiments of the present invention will be clearly and completely described below with reference to the drawings in the embodiments of the present invention. Obviously, the described embodiments are part of the embodiments of the present invention, not all of the embodiments. Based on the embodiments of the present invention, all other embodiments obtained by those skilled in the art without making inventive efforts should be included within the scope of the present invention.

It should be understood that, when used in this specification and the scope of the claims, the terms "comprising" and "including" refer to the presence of a stated feature, whole, step, operation, element, and/or component, but does not exclude the presence or addition of one or more other features, wholes, steps, operations, elements, components and/or combinations of these.

It should also be understood that the terms used in the specification of the present invention is only used to describe particular embodiments but not intended to limit the present invention. As used in this specification and the claims, the singular forms "a," "an," and "the" are intended to include the plural forms unless the context clearly dictates otherwise.

It should further be understood that the terms "and/or" used in the specification and the claims refer to any and all possible combinations of one or more of the associated listed items, and include these combinations.

The present invention provides a medical image paging display system configured to sequentially display a set of medical images and show on a display interface a page number bar representing an image display progress, wherein the location of a cursor on the page number bar represents the page number of a medical image. When the cursor moves up and down slowly on the page number bar, the pages of the medical images will be continuously changed as if playing a movie. When the cursor moves to a fixed location quickly, it can directly jump to the medical image with the page number corresponding to the fixed location and display it.

Figure 1:
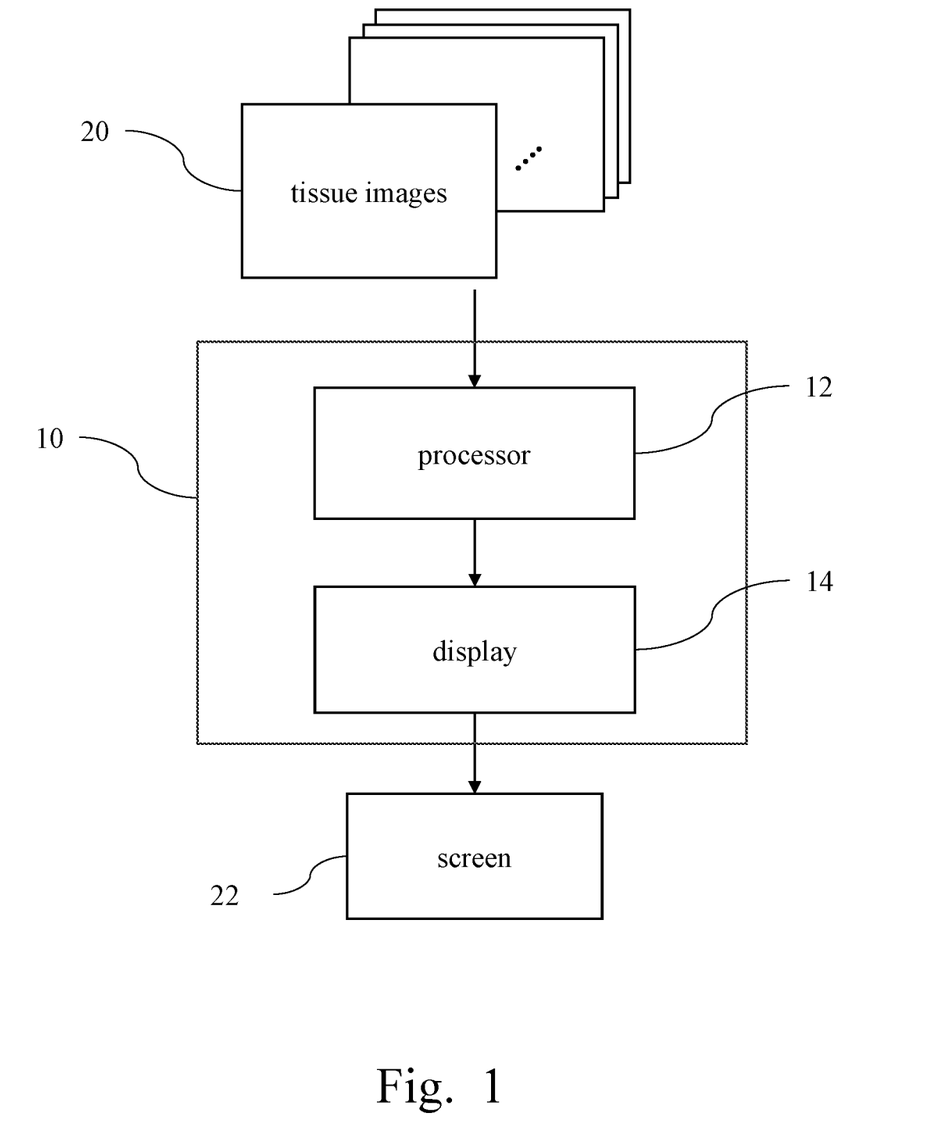
FIG. 1 is a schematic diagram illustrating a medical image paging display system according to an embodiment of the present invention.

Please refer to FIG. 1. FIG. 1 is a schematic diagram illustrating a medical image paging display system 10 according to an embodiment of the present invention. The medical image paging display system 10 includes at least one processor 12 and a display 14. The display 14 is coupled to the processor 12. The processor 12 receives external tissue images 20 and identifies at least one feature point of the tissue images 20 based on an artificial intelligence model. The tissue images 20 are continuous computed tomography images of a specific tissue. In an embodiment, the tissue images 20 are Digital Imaging and Communications in Medicine (DICOM) images. The feature point represents the abnormal tissue of the tissue image 20, such as a nodule. The processor 12 sequentially numbers the tissue images 20 to respectively have page numbers and determines whether each tissue images 20 has a feature point. Each tissue image 20 does not necessarily have the feature point. The processor 12 creates mark information corresponding to the feature point, including those of the coordinates, size, and shape of the feature point. The processor 12 further creates a page number bar and a cursor and at least one feature-page mark on the page number bar.

The mark information is implemented with a text file. The processor 12 converts the mark information into at least one feature layer for graphical display. In an embodiment, the mark information is implemented with a json text file. The processor 12 converts the mark information implemented with a json text file in a Grayscale Softcopy Presentation State (GSPS) into the feature layer. The feature layer 20) includes the mark information, the page number bar, the cursor, and the feature-page mark. The page number bar has a fixed length that fits the size of the screen. The processor 12 correspondingly marks scales on the page number bar according to the number of the tissue images 20. For example, the scales are spaced at 10 tissue images 20 and marked on the page number bar. The location of the cursor on the page number bar corresponds to the page number of the tissue image 20. For example, there are 200 tissue images 20 in all. The middle location of the page number bar represents the 100th tissue image 20. The initial coordinate and the final coordinate of the page number bar are respectively 0 and 1. The page number bar has a coordinate of ¼ that represents the $50^{th}$ tissue image 20. By the same token, the feature-page mark corresponds to the tissue image 20 having the feature point. The processor 12 applies the feature layer to the tissue images 20.

The display 14 is configured to show on a screen 22 the feature layer and the tissue images applied with the feature layer. The display 14 shows on the screen 22 the tissue image 20 corresponding to the location of the cursor on the page number bar when the cursor moves on the page number bar. For example, there are 200 tissue images 20 in all. The cursor points to the 100th tissue image 20 and the screen 22 shows the 100th tissue image 20 when the cursor moves to the middle location of the page number bar. The display 14 shows on the screen 22 the tissue image 20 corresponding to the feature-page mark when the cursor moves to the feature-page mark.

Figure 2:
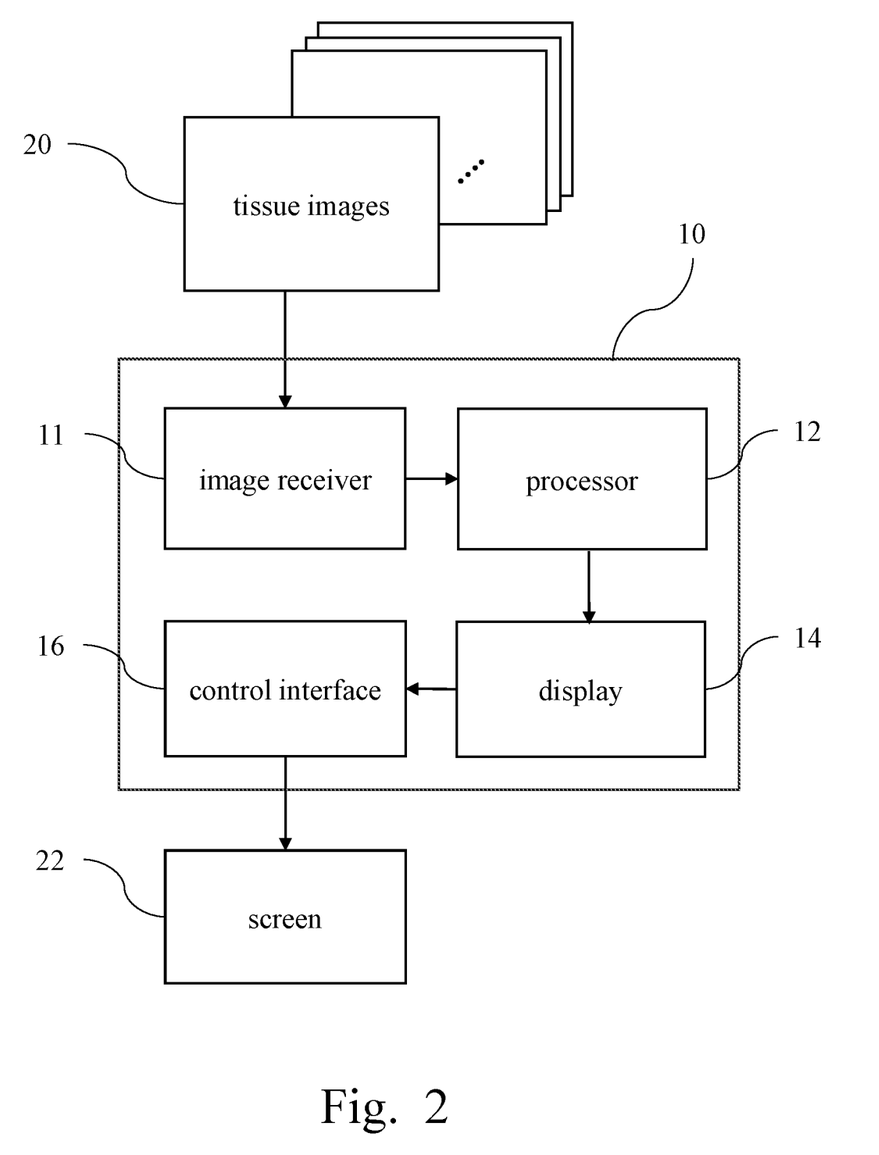
FIG. 2 is a schematic diagram illustrating a medical image paging display system according to another embodiment of the present invention.

FIG. 2 is a schematic diagram illustrating a medical image paging display system according to another embodiment of the present invention. Referring to FIG. 2, the medical image paging display system 10 includes an image receiver 11, the processor 12, the display 14, and a control interface 16. The image receiver 11 is coupled to the processor 12. The control interface 16 is coupled to the display 14 and the screen 22. The image receiver 11 is configured to receive and transmit the tissue images 20 provided by an external device to the processor 12. Thus, the processor 12 receives the tissue images 20 to identify the feature point, create the text file, and convert and apply the feature layer. The image receiver 11 receives an image package of the tissue images 20 and disassembles the image package into tissue images 20. The control interface 16 is controlled. The control interface 16 controls the cursor to move on the page number bar. For example, the control interface 16 is controlled by a mouse to control the cursor to move on the page number bar.

Figure 3:
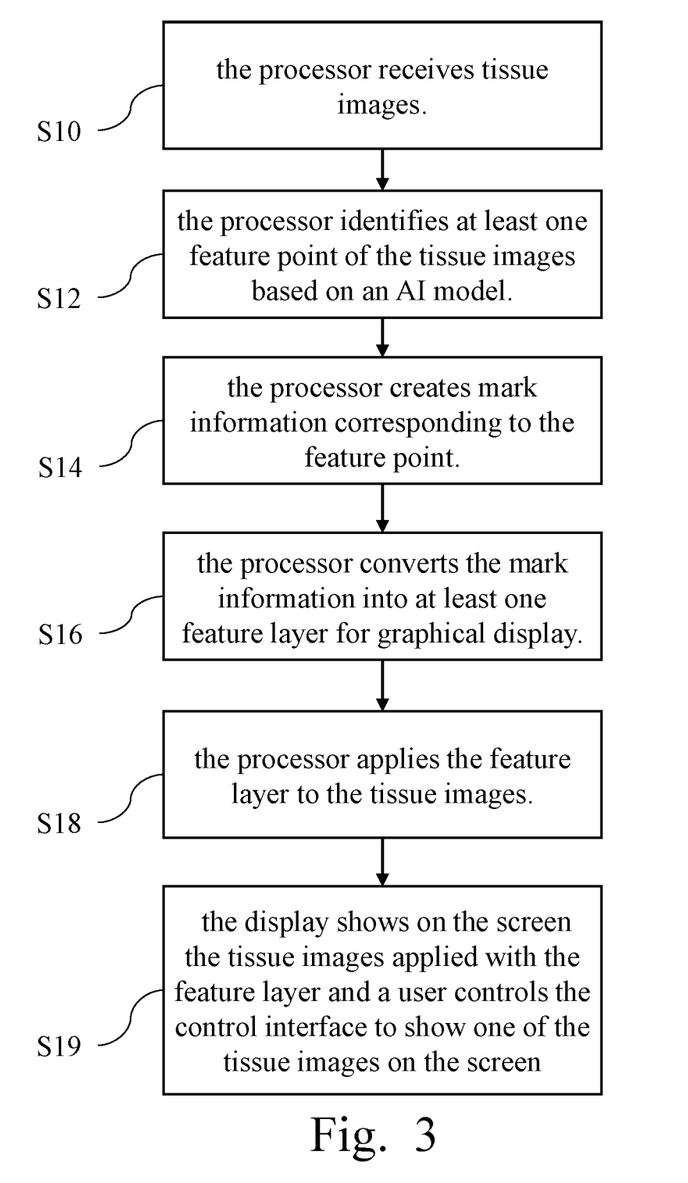
FIG. 3 is a flowchart of employing a medical image paging display system according to an embodiment of the present invention.

Please refer FIG. 2 and FIG. 3. FIG. 3 is a flowchart of employing a medical image paging display system according to an embodiment of the present invention. In Step S10, the processor 12 receives tissue images 20. Steps S12~S18 are performed by the processor 12. In Step S12, the processor 12 identifies at least one feature point of the tissue images 20 based on an artificial intelligence (AI) model. In Step S14, the processor 12 creates mark information corresponding to the feature point, wherein the mark information is implemented with a text file. In Step S16, the processor 12 converts the mark information into at least one feature layer for graphical display, wherein the feature layer includes the mark information, a page number bar, and a cursor and at least one feature-page mark on the page number bar. In Step S18, the processor 12 applies the feature layer to the tissue images 20. Finally, in Step S19, the display 14 shows on the screen 22 the tissue images 20 applied with the feature layer and a user controls the control interface 16 to show one of the tissue images 20 on the screen 22.

Figure 4:
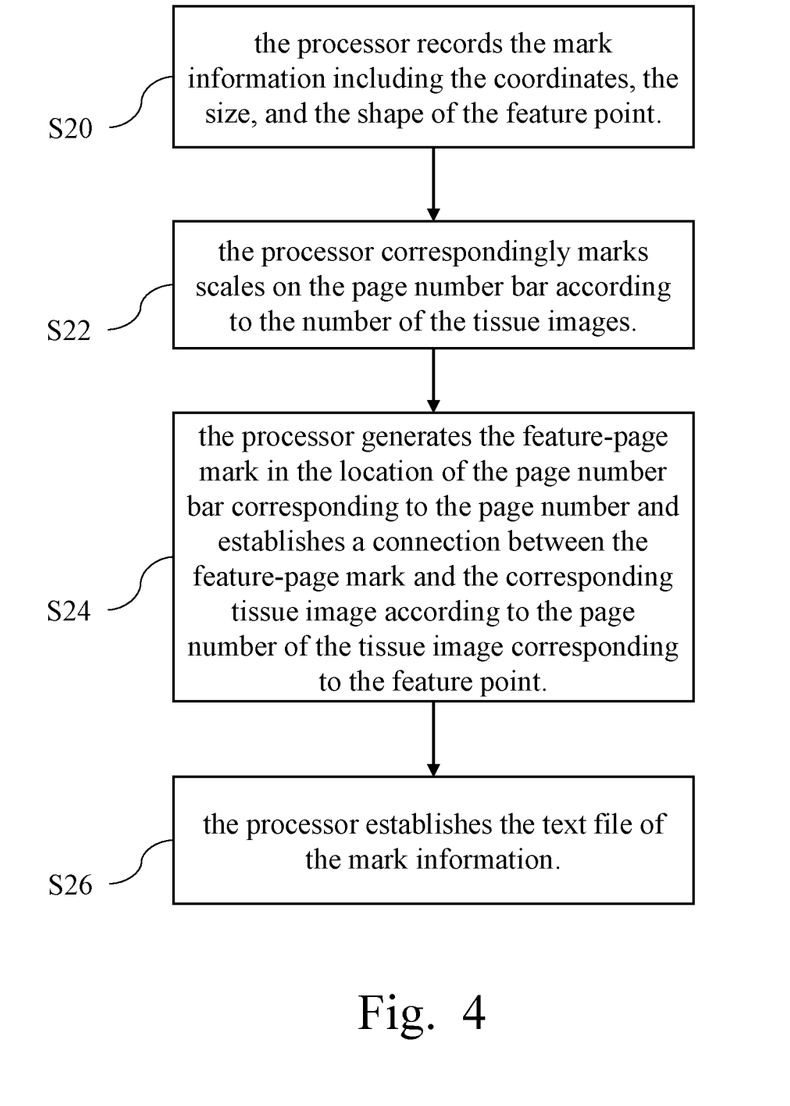
FIG. 4 is a flowchart of employing a medical image paging display system to create the text file of a feature point according to an embodiment of the present invention.

FIG. 4 is a flowchart of employing a medical image paging display system 10 to create the text file of a feature point according to an embodiment of the present invention. Firstly, in Step S20, the processor 12 records the mark information corresponding to the feature point identified by the AI model, wherein the mark information includes the coordinates, the size, and the shape of the feature point. In Step S22, the processor 12 correspondingly marks scales on the page number bar according to the number of the tissue images 20. When the number of the tissue images 20 is less than 300, the scales are spaced at 10 tissue images 20. When the number of the tissue images 20 is greater than 300, the scales are spaced at 50 tissue images 20. In Step S24, the processor 12 generates the feature-page mark in the location of the page number bar corresponding to the page number and establishes a connection between the feature-page mark and the corresponding tissue image 20 according to the page number of the tissue image corresponding to the feature point. Finally, in Step S26, the processor 12 establishes the text file of the mark information. This way, when the text file is converted into the feature layer for graphical display, the page number bar with scales is produced and the feature-page mark is marked on the page number bar.

The purpose of establishing a connection between the feature-page mark and the corresponding tissue image 20 in Step S24 is that the processor 12 automatically search for the tissue image 20 corresponding to the feature-page mark and the display 14 shows the tissue image 20 on the screen 22 when the control interface 16 receives the operation signal of clicking on the feature-page mark.

Figure 5:
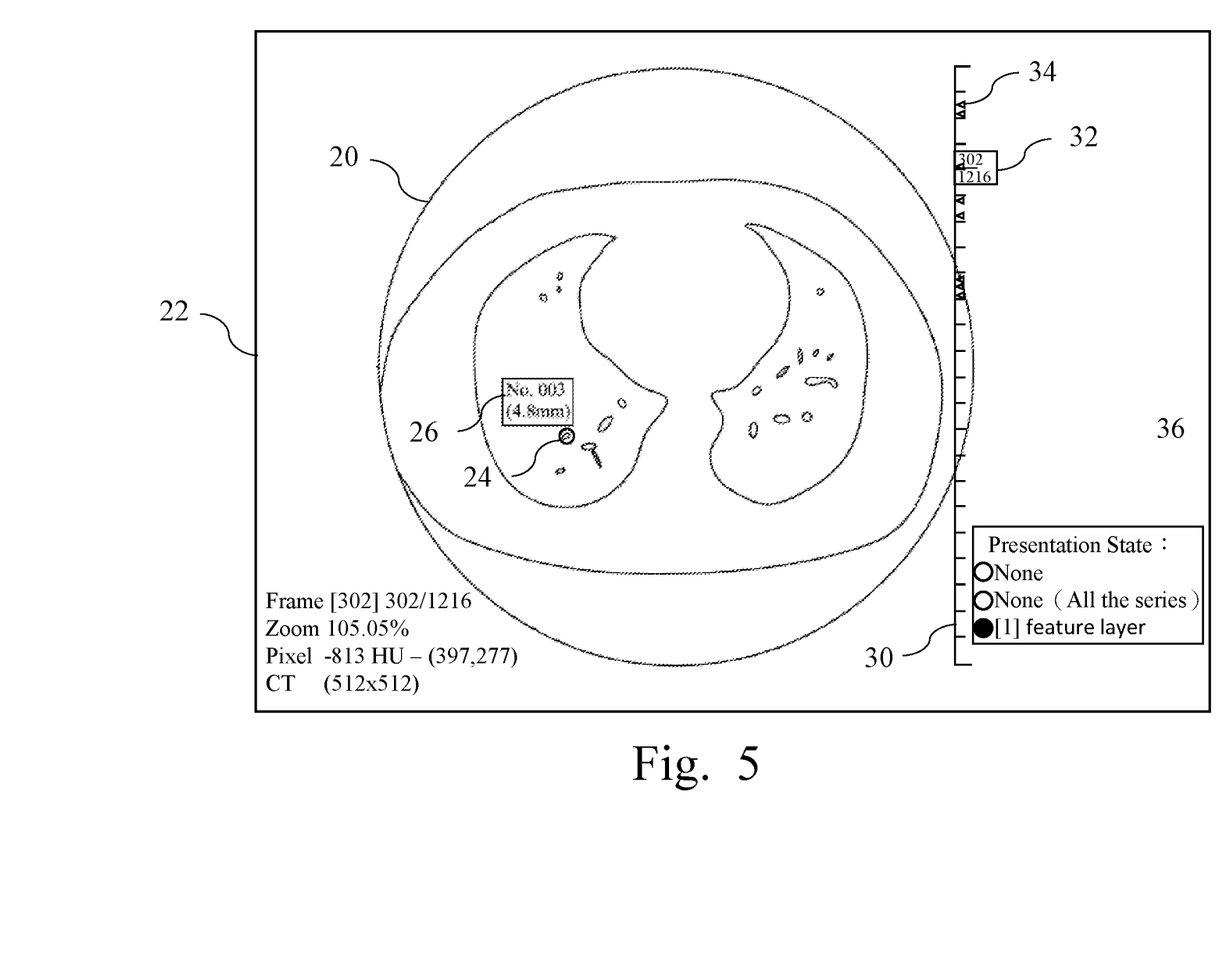
FIG. 5 is a diagram illustrating a tissue image according to an embodiment of the present invention.

Please refer to FIG. 2 and FIG. 5. FIG. 5 is a diagram illustrating a tissue image according to an embodiment of the present invention. The medical image paging display system 10 receive an image package. In the embodiment, the image package includes 1216 tissue images 20. In addition to a tissue image 20, the screen 22 shows a feature layer. The feature layer includes a page number bar 30, a feature point 24, a feature-page mark 34, and a cursor 32. The page number bar 30 is provided with scales. The cursor 32 on the page number bar 30 represents that the screen 22 currently shows the 302th one of the 1216 tissue images 20. The feature point 24 is circled by the AI model. The processor 12 marks feature-point information 26 beside the feature point 24, including those of the number and the size of the feature point 24. A feature-page mark 34 on the page number bar 30 is denoted by a triangle, which corresponds to the tissue image 20 with the feature point 24. For example, the location of the page number bar 30 corresponding to the 302th tissue image 20 is marked with the feature-page mark 34 when the 302th tissue image 20 has one feature point 24. The lower left corner of the screen 22 also presents information related to the tissue image 20, including those of page number, scale of zooming in or out image, image pixel, image size, etc. CT represents the computed tomography of the tissue image 20.

In an embodiment of the present invention, there are feature layers having different display contents. As illustrated in FIG. 5, the display 14 shows a layer field 36. The control interface 16 controls the screen 22 and the layer field 36 to present the selected feature layer.

When the cursor 32 moves on the page number bar 30, the screen 22 shows the tissue image 20 corresponding to the location of the cursor 32 on the page number bar 30. When the cursor 32 moves to the feature-page mark 34, the screen 22 shows the tissue image 20 corresponding to the feature-page mark 34. As a result, with the medical image paging display system 10 of the present invention, the pages of the tissue images 20 are continuously changed as if playing a movie, which is convenient for the doctor to move the cursor 32 up and down to watch the tissue image 20 taken from a similar angle. In addition, the tissue image 20 marked with the feature point 24 can be quickly found without spending time searching tissue images 20 one by one to find the feature points 24, which can greatly improve the efficiency of doctors and reduce the error rate of manual operations.

In conclusion, the medical image paging display system provided by the present invention arranges the feature-page mark on the page number bar according to the number of tissue images and the page number where the feature point is located, and creates a corresponding relationship between the feature-page mark and the tissue image with the feature point. When you attempt to directly click on the feature-page mark, the cursor can quickly move to the feature-page mark and the tissue image corresponding to the feature-page mark is simultaneously displayed, so that the doctor does not need to search for feature points one by one, which can improve the doctor's working efficiency and reduce misjudgment and fatigue caused by watching hundreds or even thousands of images.

The embodiments described above are only to exemplify the present invention but not to limit the scope of the present invention. Therefore, any equivalent modification or variation according to the shapes, structures, features, or spirit disclosed by the present invention is to be also included within the scope of the present invention.

What is claimed is:

1. A medical image paging display system comprising:
  at least one processor configured to:
    identify at least one feature point of tissue images based on an artificial intelligence model and create mark information corresponding to the at least one feature point, wherein the tissue images are sequentially numbered to respectively have page numbers;
    convert the mark information into at least one feature layer for graphical display, wherein the at least one feature layer comprises the mark information, a page number bar, and a cursor and at least one feature-page mark on the page number bar, wherein a location of the cursor on the page number bar corresponds to the page number of the tissue images, and the at least one feature-page mark corresponds to the tissue image having the at least one feature point; and apply the at least one feature layer to the tissue images; and a display coupled to the at least one processor and configured to show on a screen the tissue images applied with the at least one feature layer;

wherein the display shows on the screen the tissue image corresponding to the location of the cursor on the page number bar when the cursor moves on the page number bar;

wherein the display shows on the screen the tissue image corresponding to the at least one feature-page mark when the cursor moves to the at least one feature-page mark.

2. The medical image paging display system according to claim 1, further comprising an image receiver coupled to the at least one processor and configured to receive and transmit the tissue images provided by an external device to the at least one processor.

3. The medical image paging display system according to claim 2, wherein the image receiver is configured to receive an image package of the tissue images.

4. The medical image paging display system according to claim 1, wherein the mark information comprises coordinates, a size, and a shape of the at least one feature point.

5. The medical image paging display system according to claim 1, wherein the at least one processor is configured to create and convert the page number bar, the cursor, and the at least one feature-page mark into a part of the at least one feature layer.

6. The medical image paging display system according to claim 1, wherein the at least one processor is configured to correspondingly mark scales on the page number bar according to number of the tissue images.

7. The medical image paging display system according to claim 1, wherein the at least one processor is configured to generate the at least one feature-page mark in a location of the page number bar corresponding to the page number and establish a connection between the at least one feature-page mark and a corresponding the tissue image according to the page number of the tissue image corresponding to the at least one feature point.

8. The medical image paging display system according to claim 1, wherein the tissue images are Digital Imaging and Communications in Medicine (DICOM) images.

9. The medical image paging display system according to claim 1, wherein the at least one processor is configured to convert the mark information implemented with a json text file in a Grayscale Softcopy Presentation State (GSPS) into the at least one feature layer.

10. The medical image paging display system according to claim 1, wherein the at least one feature layer comprises a plurality of feature layers having different display contents.

11. The medical image paging display system according to claim 1, further comprising a control interface coupled to the at least one processor and the display and configured to control the cursor to move on the page number bar.

12. The medical image paging display system according to claim 11, wherein the display is further configured to show a layer field and the control interface is configured to control the layer field to present a selected the at least one feature layer.

* * * * *